(12) United States Patent
Justis (10) Patent No.: US 7,455,685 B2
(45) Date of Patent: Nov. 25, 2008

(54) INSTRUMENTS AND METHODS FOR SECURING A CONNECTING ELEMENT ALONG A BONY SEGMENT

(75) Inventor: Jeff R. Justis, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 650 days.

(21) Appl. No.: 10/674,036

(22) Filed: Sep. 29, 2003

(65) Prior Publication Data
US 2005/0070917 A1 Mar. 31, 2005

(51) Int. Cl.
A61B 17/70 (2006.01)
(52) U.S. Cl. ..................................... 606/246
(58) Field of Classification Search ................ 606/53, 606/54, 59, 60, 61, 99, 104
See application file for complete search history.

(56) References Cited

U.S. PATENT DOCUMENTS

| 2,338,159 | A |   | 1/1944  | Appleton         |         |
|-----------|---|---|---------|------------------|---------|
| 3,299,883 | A | * | 1/1967  | Rubens           | 600/102 |
| 4,335,715 | A |   | 6/1982  | Kirkley          |         |
| 4,545,374 | A |   | 10/1985 | Jacobson         |         |
| 4,570,624 | A |   | 2/1986  | Wu               |         |
| 4,573,448 | A |   | 3/1986  | Kambin           |         |
| 4,722,331 | A |   | 2/1988  | Fox              |         |
| 4,883,048 | A |   | 11/1989 | Purnell et al.   |         |
| 4,896,661 | A |   | 1/1990  | Bogert et al.    |         |
| 4,955,885 | A |   | 9/1990  | Meyers           |         |
| 5,067,954 | A | * | 11/1991 | Ilizarov         | 606/58  |
| 5,163,940 | A |   | 11/1992 | Bourque et al.   |         |
| 5,242,443 | A |   | 9/1993  | Kambin           |         |
| 5,242,444 | A |   | 9/1993  | MacMillan        |         |
| 5,281,223 | A |   | 1/1994  | Ray              |         |
| 5,334,205 | A |   | 8/1994  | Cain             |         |
| 5,383,454 | A |   | 1/1995  | Bucholz          |         |
| 5,437,667 | A |   | 8/1995  | Papierski et al. |         |

(Continued)

FOREIGN PATENT DOCUMENTS

DE 197 26 754 A1 6/1997

(Continued)

OTHER PUBLICATIONS

Sofamor Danek; *The Spine Specialist, TSRH Pedicle Screw Spinal System, Severe Spondylolisthesis of L5-S1 Grade 3 & 4*; Surgical Technique as described by Edward H. Simmons, MD, Edward D. Simmons, Jr. MD, Howard D. Markowitz, MD © 1997.

(Continued)

*Primary Examiner*—Eduardo C Robert
*Assistant Examiner*—Nicholas Woodall
(74) *Attorney, Agent, or Firm*—Krieg Devault LLP (57) ABSTRACT

Instruments and methods include a guide instrument mountable to at least one anchor extension to guide the positioning of an anchor in a bony segment. The guide instrument facilitates aligning the anchor with one or more other anchors already engaged to the bony segment. The anchors can then be engaged with a connecting element extending therebetween. The guide instrument facilitates multi-level fixation of bony segments with bone anchors and one or more connecting elements in a minimally invasive surgical approach.

38 Claims, 7 Drawing Sheets

U.S. PATENT DOCUMENTS

| | | | |
|---|---|---|---|
| 5,569,248 A | 10/1996 | Mathews | |
| 5,591,165 A | 1/1997 | Jackson | |
| 5,591,167 A | 1/1997 | Laurain et al. | |
| 5,601,562 A | 2/1997 | Wolf et al. | |
| 5,613,971 A | 3/1997 | Lowery et al. | |
| 5,643,273 A | 7/1997 | Clark | |
| 5,681,320 A | 10/1997 | McGuire | |
| 5,704,937 A | 1/1998 | Martin | |
| 5,720,751 A | 2/1998 | Jackson | |
| 5,725,532 A | 3/1998 | Shoemaker | |
| 5,735,857 A | 4/1998 | Lane | |
| 5,741,266 A | 4/1998 | Moran et al. | |
| 5,752,962 A | 5/1998 | D'Urso | |
| 5,772,594 A | 6/1998 | Barrick | |
| D401,335 S * | 11/1998 | Koros et al. | D24/133 |
| 5,851,183 A | 12/1998 | Bucholz | |
| 5,871,445 A | 2/1999 | Bucholz | |
| 5,891,034 A | 4/1999 | Bucholz | |
| 5,891,150 A | 4/1999 | Chan | |
| 5,891,158 A | 4/1999 | Manwaring et al. | |
| 5,910,141 A | 6/1999 | Morrison et al. | |
| 6,036,692 A | 3/2000 | Burel et al. | |
| 6,099,528 A | 8/2000 | Saurat | |
| 6,123,707 A | 9/2000 | Wagner | |
| 6,226,548 B1 | 5/2001 | Foley et al. | |
| 6,235,028 B1 | 5/2001 | Brumfield et al. | |
| 6,530,929 B1 | 3/2003 | Justis et al. | |
| 7,118,576 B2 * | 10/2006 | Gitis et al. | 606/87 |
| 2002/0045904 A1 | 4/2002 | Fuss et al. | |
| 2002/0161368 A1 * | 10/2002 | Foley et al. | 606/61 |
| 2005/0021031 A1 * | 1/2005 | Foley et al. | 606/61 |
| 2005/0038432 A1 * | 2/2005 | Shaolian et al. | 606/61 |
| 2005/0234449 A1 * | 10/2005 | Aferzon | 606/61 |
| 2006/0149238 A1 * | 7/2006 | Sherman et al. | 606/61 |

FOREIGN PATENT DOCUMENTS

| | | |
|---|---|---|
| EP | 0 858 780 A2 | 8/1998 |
| JP | 06-105852 A | 4/1994 |
| SU | 0839513 | 6/1981 |
| WO | WO 97/30666 | 8/1997 |
| WO | WO 97/38639 | 10/1997 |
| WO | WO 99/15097 | 4/1999 |
| WO | WO 99/26549 | 6/1999 |
| WO | WO 00/44288 | 8/2000 |

OTHER PUBLICATIONS

Sofamor Danek, The Spine Specialist; *Horizon Spinal System, Surgical Technique*; as described by Samuel J. Laufer, M.D., J. Andrew Bowe, M.D. © 1999.

Posterior Percutaneous Spine Instrumentation; 9 Supp 1) Eur Spine J (2000) Received Sep. 3, 1999 Accepted Sep. 4, 1999.

\* cited by examiner

INSTRUMENTS AND METHODS FOR SECURING A CONNECTING ELEMENT ALONG A BONY SEGMENT

BACKGROUND

Various devices and methods for stabilizing bony segments have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony segment and secured to the bony segment to stabilize the components relative to one another. The components of the bony segment are exposed and one or more bone engaging fasteners are placed into each component. The elongated rod is then secured to the bone engaging fasteners in order to stabilize the components of the bony segment.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations within the body and the potential trauma to vital intervening tissues. The development of percutaneous minimally invasive spinal procedures has yielded a major improvement in reducing trauma, recovery time and post-operative pain. The benefits of minimally invasive techniques have also found application in surgeries for other locations in the body where it is desirable to minimize tissue disruption.

While minimally invasive techniques have yielded benefits, there remains a need for instruments and methods that facilitate minimally invasive stabilization of bony segment.

SUMMARY

The present invention relates to instruments and methods for securing a connecting element to a bony segment of an animal subject. The instruments and methods can be employed in minimally invasive surgical procedures.

In one aspect of the invention, there is provided a guide instrument attachable to an anchor extension extending from a bone anchor engaged to a bony segment. The guide instrument is includes a guide member movable relative to the anchor extension to guide placement of a second anchor in the bony segment in a position relative to the first anchor that facilitates engagement of a connecting element to each of the anchors.

In another aspect, a method for engaging a secondary anchor to a bony segment includes: engaging first and second primary anchors to the bony segment; mounting a guide instrument to the first and second primary anchors; and guiding the secondary anchor to the bony segment with the guide instrument to position a secondary anchor along an alignment axis extending between the first and second primary anchors.

Related features, aspects, embodiments, objects and advantages of the present invention will be apparent from the following description.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Instruments and methods are provided for placement of a secondary anchor in a bony segment in a desired position relative to at least one primary anchor engaged with the bony segment, and to locate at least a portion of the secondary anchor along an alignment axis. A connecting element is positionable between the primary and second anchors and along the alignment axis to connect the primary and secondary anchors to one another. The instruments and methods position at least a receiver portion of the primary and secondary anchors along the alignment axis prior to positioning the connecting element between the primary and secondary anchors. Accordingly, insertion of the connecting element between the primary and secondary anchors is facilitated since the receiver portions of the primary and second anchors are pre-aligned along the axis in which the connecting element will be positioned.

The instruments include a guide instrument mountable to at least one primary anchor and movable relative thereto. The guide instrument includes a guide member positionable to orient a guide axis at any one of a number of orientations relative to the alignment axis that intersect the alignment axis. The guide instrument can be employed to guide any one or combination of a drill, a tap, and a secondary anchor to a desired orientation relative to the alignment axis, with a receiving portion of the secondary anchor positioned along the alignment axis. After placement of the secondary anchor, a connecting element is positioned along the alignment axis to a location where it is engageable to the primary and second anchors to stabilize the bony segment.

In one application, the guide instrument is mounted between first and second anchor extensions extending from first and second primary anchors. As used herein, primary anchor identifies an anchor engaged to the bony segment prior to placement of the secondary anchor with the guide instrument. The alignment axis extends between receiving portions of the primary anchors along the bony segment. The guide instrument includes an adjustable guide member that defines a guide axis that intersects the alignment axis. When mounted to the anchor extensions of the primary anchors, the guide member can be repositioned to provide a desired trajectory for the secondary anchor into the bony segment. At any position of the guide member, the guide axis intersects the alignment axis.

Thus, drilling and tapping, if necessary, and engagement of the secondary anchor into the bony segment is controlled so that a receiving portion of the secondary anchor is aligned with the receiving portions of the primary anchors along the alignment axis while the trajectory of the secondary anchor into the bony segment can vary from that of one or both of the primary anchors. While it is contemplated that the secondary anchor is positioned between the primary anchors, it is further contemplated that the second anchor can be positioned to provide an extension of the alignment axis extending between the primary anchors. It is also contemplated that the guide instrument can be employed to align receiver portions of two anchors, three anchors, or four or more anchors.

Figure 1:
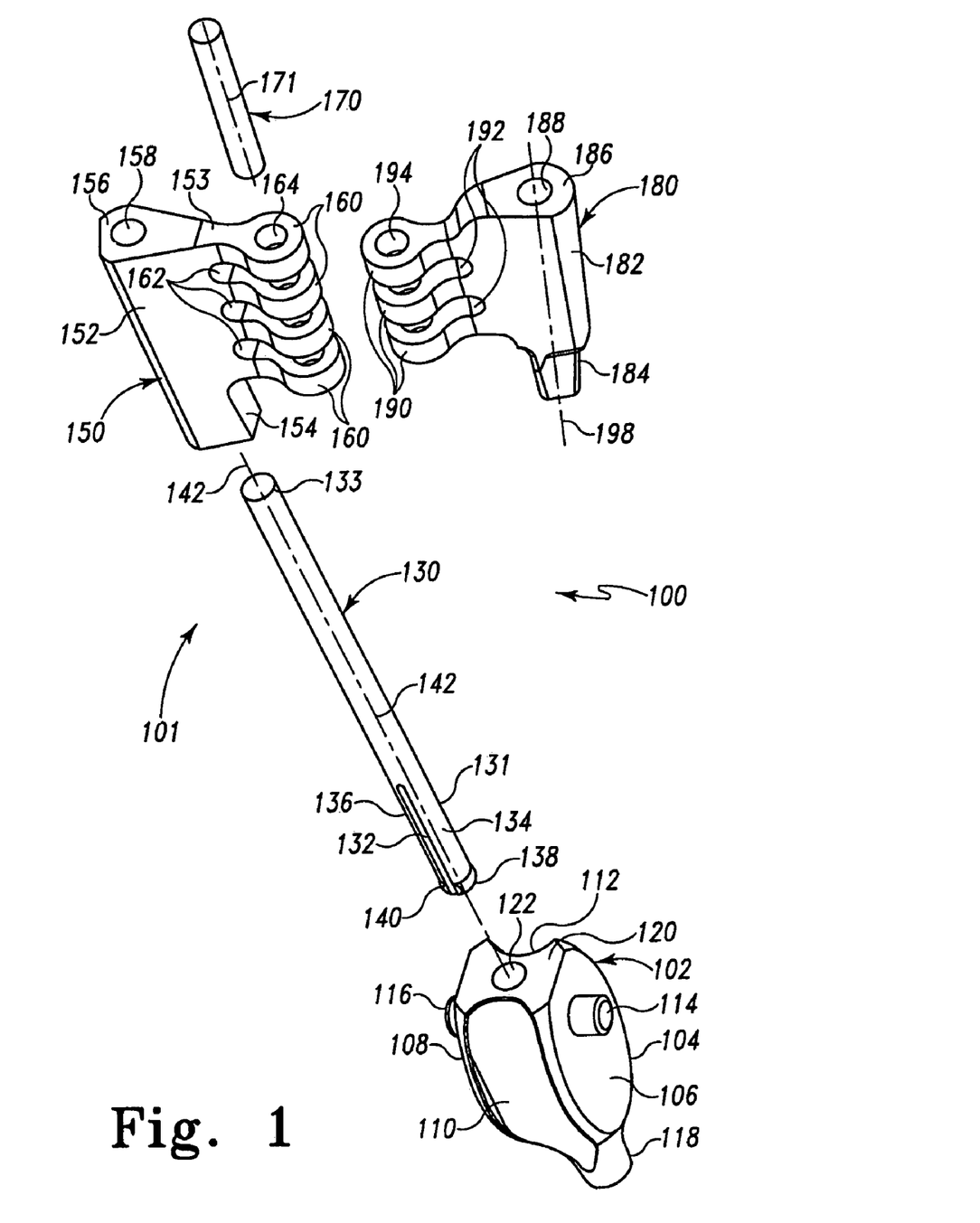
FIG. 1 is an exploded perspective view of a guide instrument.

Referring to FIG. 1, one embodiment of a guide instrument 100 is shown in an exploded perspective view. Guide instrument 100 includes a mounting assembly 101 extending along a mounting axis 142. Mounting assembly 101 includes a mounting member 102 and a coupling member 150. A mounting pin 130 extends between and rotatably couples coupling member 150 to mounting member 102. Mounting member 102 is engageable between anchor extensions 40 of a pair of primary anchors, as shown in FIGS. 4-9.

A guide member 180 is pivotally coupled to coupling member 150 with a hinge pin 170 along a hinge axis 171. Coupling member 150 is movable about a rotational center defined by mounting axis 142 to position hinge axis 171 and thus guide member 180 at any one of a number of positions about mounting member 102. Guide member 180 defines a guide axis 198, which can be positioned by pivoting guide member 180 relative to coupling member 150 about hinge axis 171 and/or by rotating coupling member 150 about mounting axis 142. The adjustable positioning provided by coupling member 150 and guide member 180 allows a secondary anchor to be positioned into the bony segment at a desired trajectory defined by guide axis 198. Coupling member 150 and guide member 180 are structured so that guide axis 198 intersects alignment axis 200 at any position of coupling member 150 and guide member 180 about mounting axis 142.

Figures 6, 8:
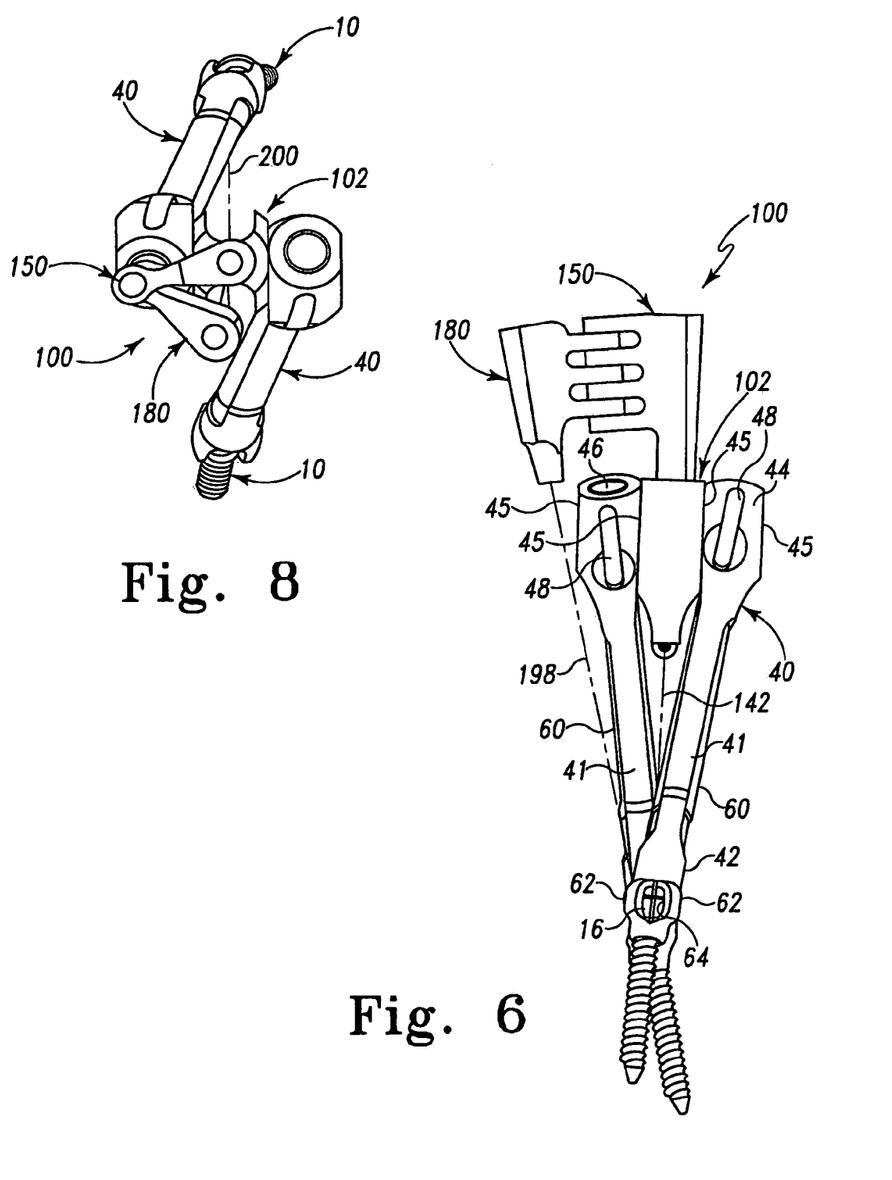
FIG. 6 is a right hand elevation view of the instrument, extensions and anchors of FIG. 4.
FIG. 8 is a top plan view of the guide instrument, extensions and anchors of FIG. 4 with the guide instrument repositioned relative to the anchor extensions.
Figures 7, 9:
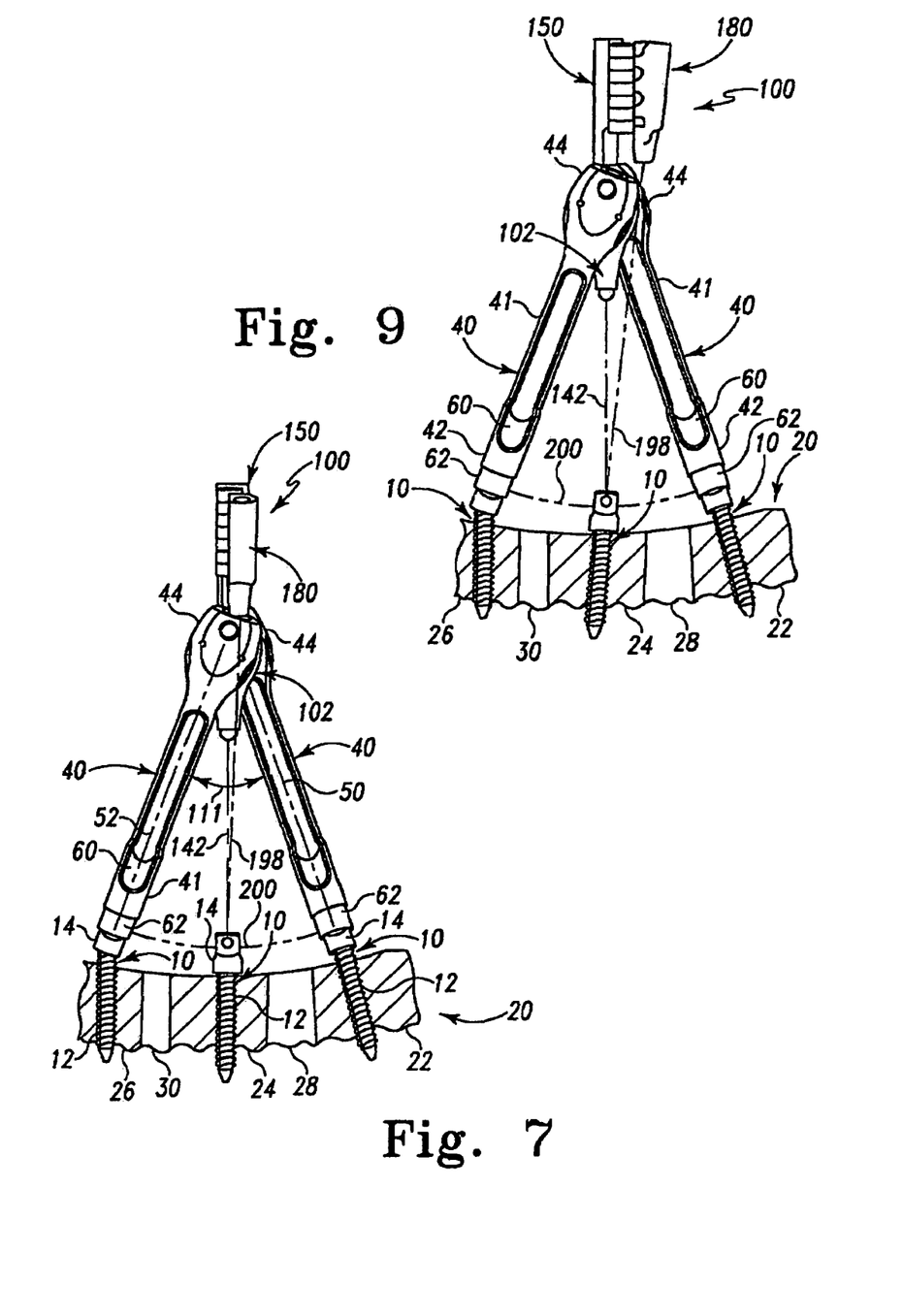
FIG. 7 is a frontal elevation view of the instrument, extensions and anchors of FIG. 4 mounted to a spinal column segment.
FIG. 9 is a frontal elevation view of the instrument, extensions and anchors of FIG. 8 mounted to a spinal column segment.

Mounting member 102 includes a body 104 comprising opposite first and second sides 106, 108 and opposite third and fourth sides 110, 112. A first mounting pin 114 extends from first side 106, and a second mounting pin 116 extends from second side 108. Body 104 further includes a tapered distal end 118 and a proximal end wall 120. A bore 122 extends through body 104 and opens at proximal end wall 120 and distal end 118. Third and fourth sides 110, 112 can include a concave surface profile to accommodate passage of drill, tap or driving instruments along mounting member 102 when guide member 180 is positioned so that guide axis 198 is adjacent thereto, as shown in FIGS. 8 and 9.

Mounting pins 114, 116 are positionable in receptacles formed in sidewalls 45 adjacent the proximal ends 44 of anchor extensions 40 to mount guide instrument 100 thereto with mounting axis 142 intersecting alignment axis 200. Mounting member 102 can be pivoted about mounting pins 114, 116, as indicated by arrow 111 in FIG. 7, to adjust the location of intersection between mounting axis 142 and alignment axis 200 along the bony segment.

Coupling pin 130 extends along mounting axis 142 from a proximal end 133 to a distal end portion 131. Distal end portion 131 includes slot 132 extending therealong that opens at a distal end of pin 130. Slot 132 separates distal end portion 131 into a first finger 134 and a second finger 136. A first protrusion 138 projects radially outwardly from first finger 134, and a second protrusion 140 projects radially outwardly from second finger 136. Fingers 134, 136 can deflect toward one another for insertion through bore 122 of mounting member 102. Fingers 134, 136 are resiliently biased to return toward their pre-insertion configuration when projections 138, 140 extend distally beyond distal end 118 of mounting member 102. Projections 138, 140 engage distal end 118 of mounting member 102 to axially and releasably secure coupling pin 130 to mounting member 102.

Coupling member 150 includes a body portion 152 and a coupling portion 153 extending laterally from body portion 152. Body portion 152 extends from a distal end member 154 to a proximal end wall 156. A bore 158 extends through body portion 152 and opens at proximal end wall 156 and at a distal face of distal end member 154. Mounting pin 130 is positionable through bore 158 and engageable therein via a press fit, mechanical fastener, welding or other suitable engagement technique. Coupling pin 130 is rotatable in bore 122 of mounting member 102 so that coupling member 150 can be rotated 360 degrees about mounting member 102.

Coupling portion 153 include a number of hinge members 160 extending laterally from body portion 152. Hinge members 160 form a hinge bore 164 extending therethrough. A number of slots 162 extend between adjacent hinge members 160. Guide member 180 also includes a number of hinge members 190, which include slots 192 therebetween. A hinge bore 194 extends through hinge members 190. When guide member 180 is assembled to coupling member 150, hinge members 160, 190 interdigitate to align hinge bores 164, 194 to receive hinge pin 170. Hinge pin 170 pivotally couples guide member 180 to coupling member 150 about hinge axis 171.

Guide member 180 includes a guide body 182 extending between a distal end member 184 and a proximal end wall 186. A guide passage 188 extends along guide axis 198, and opens at the distal and proximal ends of guide body 182. Hinge members 190 extend laterally from guide body 182 such that when guide member 180 is coupled to coupling member 150, guide axis 198 is offset from the hinge axis 171 defined along hinge member 170.

When mounted to one of or each of the anchor extensions 40, as shown in FIGS. 5-9, for example, guide axis 198 can be universally rotated about mounting axis 142 with coupling member 150 to provide a desired approach to the surgical site relative to anchor extensions 40 and mounting axis 142. For example, as shown diagrammatically in FIGS. 2 and 3, coupling member 150 can be rotated 360 degrees about mounting axis 142, allowing hinge axis 171 to be positioned at any location along hinge axis path 173. At any location on hinge axis path, guide member 180 can be positioned to form a linear extension of coupling member 150, thus providing a maximum angular orientation 202 between mounting axis 142 and guide axis 198. Guide member 180 can be pivoted about hinge axis 171 from its linear extension position to a position indicated by guide members 180' or 180" to provide a minimum angular orientation 204 between guide axes 198', 198" and mounting axis 142. Guide member 180 can further be pivoted to a location between its minimum and maximum angular orientations.

Figure 2:
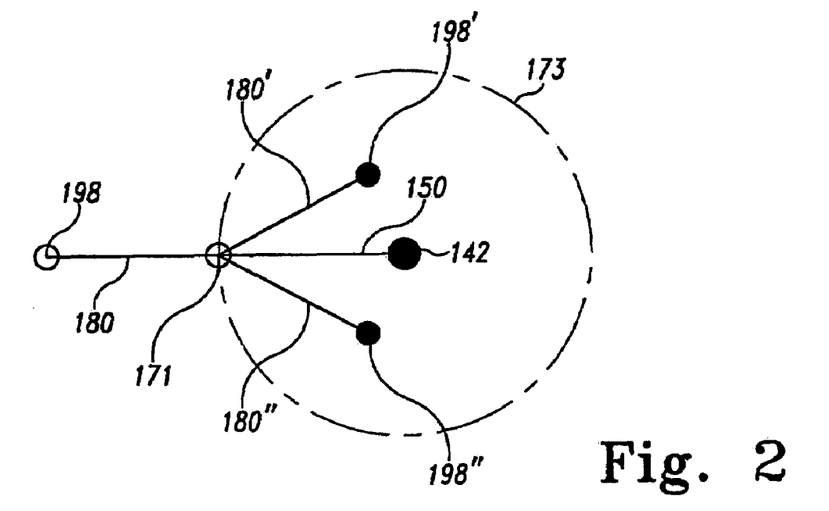
FIG. 2 is a diagrammatic plan view of a movement pattern of the guide instrument of FIG. 1.
Figure 3:
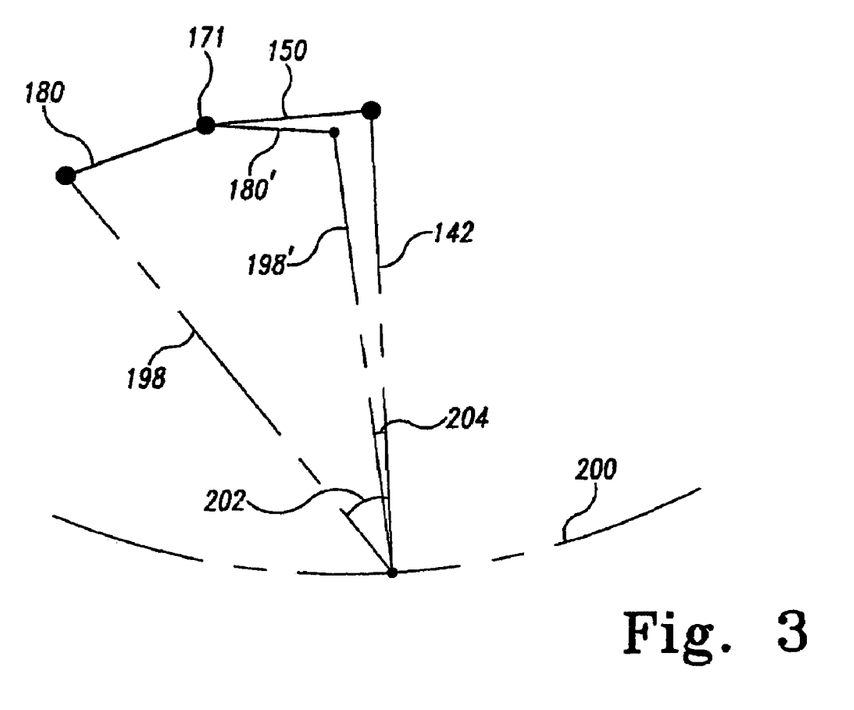
FIG. 3 is a diagrammatic elevation view of a movement pattern of the guide instrument of FIG. 1.
Figure 4:
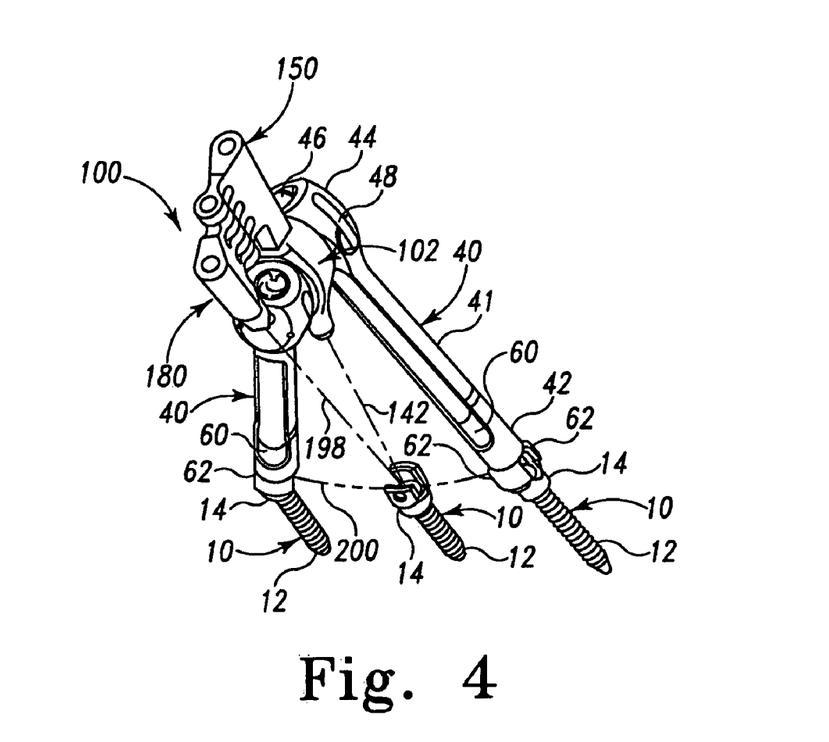
FIG. 4 is a perspective view of the guide instrument of FIG. 1 mounted to a pair of anchor extensions of an anchoring system.
Figure 5:
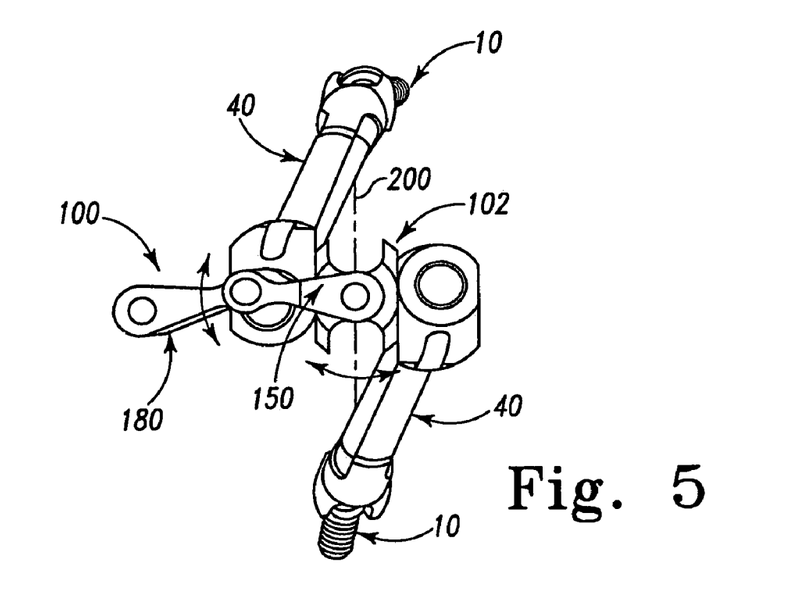
FIG. 5 is a top plan view of the guide instrument, extensions and anchors of FIG. 4.

In the positions indicated by 180', 180", guide member 180 is positioned adjacent to or in contact with body portion 152 such that further pivoting movement is limited. The recessed sides 110, 112 of mounting member 102 allow guide axis 198 to remain unobstructed in the positions indicated by 180', 180". In one embodiment, angular orientations 202, 204 range from about 2 degrees for minimum angular orientation 204 to about 8 degrees for maximum angular orientation 202. Other embodiments contemplate angular orientations ranging from 0 degrees to about 28 degrees. Further It is still further embodiments contemplate that guide axis 198 can be oriented relative to alignment axis 200 at any anatomically expected trajectory based on the anatomical location of alignment axis 200, and also based on the anatomical features for a particular patient.

Placement of the secondary anchor can further be guided along mounting axis 142 by removing coupling pin 130 from mounting body 102. In this form of guide instrument 100, drilling, tapping and driving instruments are guided through bore 122 to locations intersecting alignment axis 200. Accordingly, the secondary anchor can also be positioned at an angular orientation of 0 degrees relative to mounting axis 142.

When assembled, as shown in FIGS. 4-7 for example, guide instrument 100 can be mounted to at least one of a pair of anchor extensions 40 with mounting member 102. In the illustrated embodiment, mounting member 102 is positioned between and mounted to each of the pair of anchor extensions 40. Anchor extensions 40 are releasably mounted to respective ones of the receiver portions 14 of anchors 10. With guide member 100 mounted to anchor extensions 40, distal end member 154 extends sufficiently proximally to proximally offset hinge axis 171 from the proximal ends of anchor extensions 40 so that coupling member 150 can be rotated 360 degrees about mounting member 102. Guide member 180 can be pivoted about hinge axis 171 in either direction between positions adjacent to body portion 152 of coupling member 150 to a position forming an extension of coupling portion 153.

First and second anchor extensions 40 extend proximally from respective ones of the primary anchors 10 along a first extension axis 50 and a second extension axis 52, respectively. Anchor extensions 40 each include an outer sleeve member 41 extending between a distal portion 42 and a proximal portion 44. Proximal portion 44 includes an enlarged, bulbous configuration with flattened medial and lateral sidewalls 45 to facilitate engagement of adjacent anchor extensions 40 to one another. The medially oriented walls 45 are positioned adjacent the first and second sides 106, 108 of mounting member 102, and each includes a receptacle to rotatably receive a corresponding one of the mounting pins 114, 116. Anchor extensions 40 further include a passage 46 extending therethrough and opening proximally and also opening in the receiver portion 14 of anchor 10. Passage 46 provides a pathway for placement of a coupling member, such as a set screw, into receiver portions 14 to secure the connecting element to the respective anchor 10.

Anchor extensions 40 include an inner sleeve member 60 positioned in an outer sleeve member 41. Inner sleeve member 60 includes distal fingers 62 projecting distally from distal portion 42 of outer sleeve member 41. Distal fingers 62 can include an outer cam surface along which the distal portion 42 of outer sleeve member 41 moves to move distal fingers 62 toward and away from one another. Distal fingers 62 form a passage 64 therebetween that is alignable with a passage 16 of receiver portion 14 of anchor 10 when coupled thereto. Fingers 62 can include projections extending therefrom that are positionable in adjacent receptacles formed in the outer surface of receiver portion 14 to firmly secure anchor extension 40 thereto.

A coupling mechanism 48 extends through proximal portion 44 and releasably secures inner and outer sleeve members 60, 41 in at least first and second positions relative to one another. In a first position, shown in FIGS. 4-7, outer sleeve member 41 is distally advanced so that distal portion 42 extends along distal fingers 62 and biases them toward one another to grip receiver portion 14 of bone anchor 10 therebetween. Outer sleeve member 41 can also be moved proximally relative to inner sleeve member 60 to allow distal fingers 62 to move away from one another, releasing receiver portion 14 of bone anchor 10 from therebetween. Fingers 62 can be coupled with a proximally extending body of inner sleeve member 60 via an integral hinge, pins, or other suitable connection means that allows fingers 62 to move toward and away from one another to secure and release anchor 10 therebetween.

Figure 10:
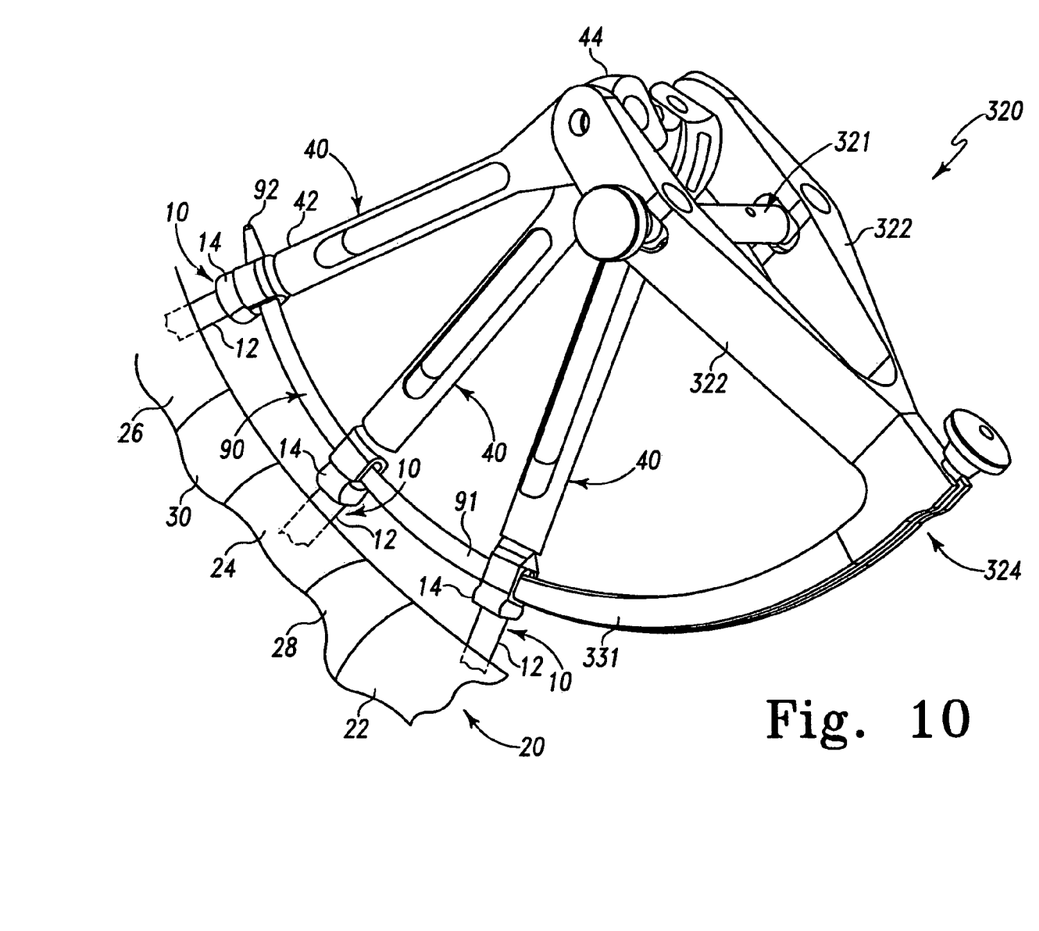
FIG. 10 is a perspective view of an inserter instrument mounted to anchor extensions and a connecting element with the connecting element positioned through receiver portions of the anchors.

In FIGS. 7, 9 and 10 there is shown a bony segment 20 to which anchors 10 are engaged to receive a connecting element 90. One application of guide instrument 10 contemplates that bony segment 20 includes a first vertebra 22, a second vertebra 24, and a third vertebra 26. A first disc space 28 is between first and second vertebrae 22, 24, and a second disc space 30 is between second and third vertebrae 24, 26.

Primary anchors 10 are engaged to each of the first vertebra 22 and third vertebra 26 using any known insertion technique. It contemplated that receiver portions 14 are multi-axial, and can be pivoted and rotated relative to the engagement portion 12 of the primary and secondary anchors 10 when the engagement portion 12 is engaged to the bony structure. Accordingly receiver portions 14 can be aligned with one another along alignment axis 200 extending between the receiver portions of the primary and secondary anchors 10. Connecting element 90 is inserted and positioned along alignment axis 200 and through passages 16 of receiver portions 14. Set screws engaged in receiver portions 14 secure connecting element 90 to the primary anchors 10, and link primary anchors 10 to another.

In one embodiment, connecting element 90 is inserted percutaneously into the patient along an insertion axis that is defined along an extension of alignment axis 200. The connecting element 90 is guided into position through passages 16 of receiver portions 14. Other embodiments contemplate other insertion paths for the connecting element, including top loading and side loading the connecting element for engagement with the anchors, and also placing the anchors through a connecting element already positioned along alignment axis 200.

After primary anchors 10 are engaged to vertebrae 22, 26, the anchor extensions 40 are manipulated through the skin and mounted to mounting member 102 of guide instrument 100. Coupling member 150 and guide member 180 are positioned to provide the desired alignment of guide axis 198 for engagement of a secondary anchor 10 to vertebra 24. A hole can be drilled into vertebra 24 and tapped, if necessary, through the guide member 180 along guide axis 198. Alternatively, a self-drilling screw can be employed and guided into vertebra 24 with guide member 180. In any event, guide instrument 100 allows placement of the secondary anchor at any one of an infinite number of selectable trajectories into vertebra 24 with receiver portion 14 of secondary anchor 10 positioned along alignment axis 200.

Figures 11, 12:
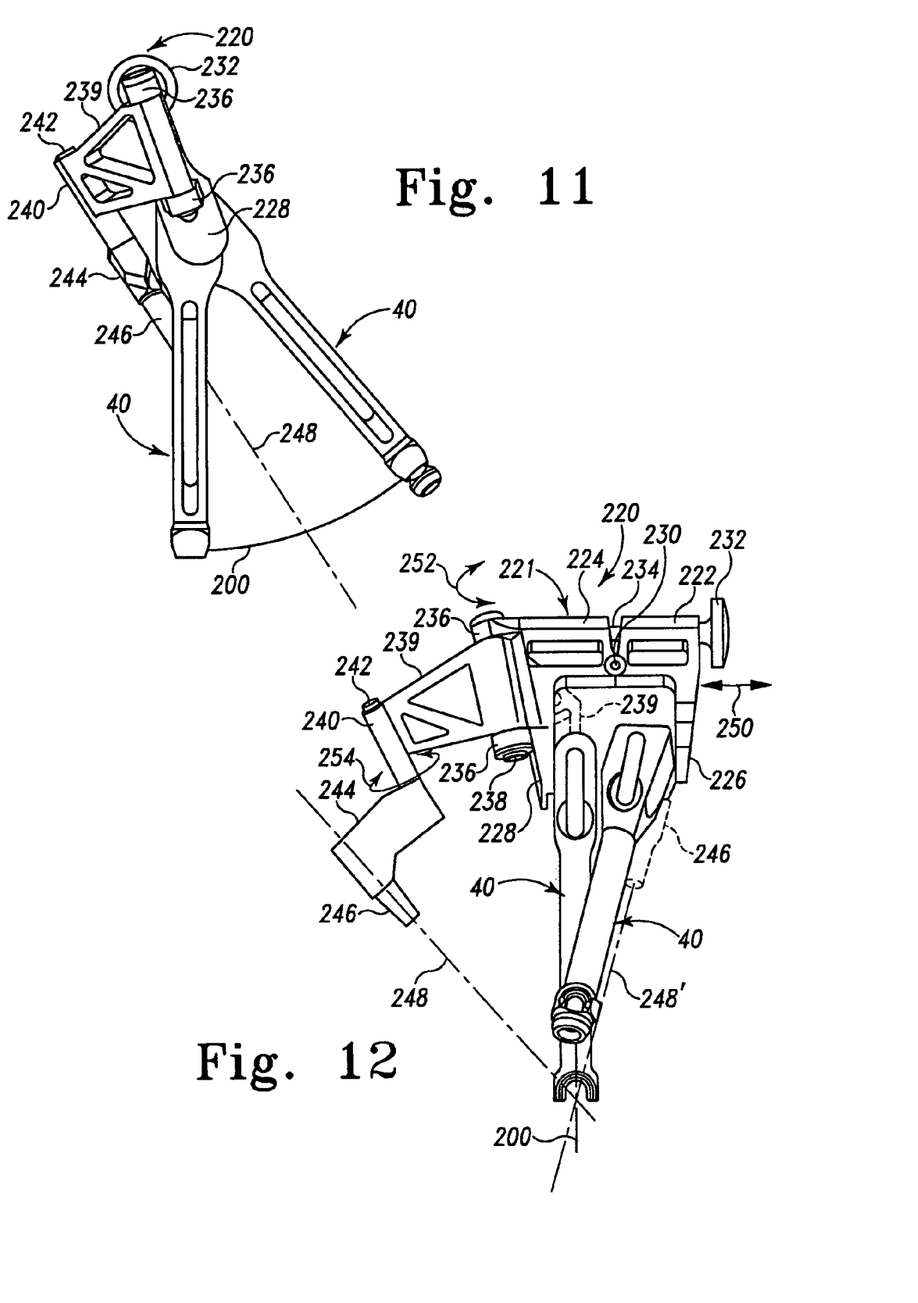
FIG. 11 is an elevation view of another embodiment guide instrument mounted to a pair of anchor extensions.
FIG. 12 is a right hand elevation view of the guide instrument and anchor extensions of FIG. 11 that further includes an alternate position for the guide instrument.

Another embodiment guide instrument 220 is shown in FIGS. 11 and 12. In contrast to guide instrument 100, guide instrument 220 is mountable to anchor extensions 40 by clamping the anchor extensions 40 to another adjacent their proximal ends. Guide instrument 220 includes a mounting assembly 221 that includes a first clamping arm 222 pivotally coupled to a second clamping arm 224. First clamping arm 222 includes a distal extension 226 engageable to a laterally oriented sidewall of first anchor extension 40 adjacent a proximal end of anchor extension 40. Second clamping arm 224 includes a distal extension 228 engageable to an oppositely facing sidewall of second anchor extension 40.

Clamping arms 222, 224 are pivotally coupled to one another at an intermediate joint 230 and pivot thereabout to clamp and release anchor extensions 40 from therebetween. A drawbar 234 is threadingly received in a passage extending through first clamping arm 222, and a distal end of draw bar 234 is engaged in second clamping arm 224. Drawbar 234 is offset proximally from intermediate joint 230. As draw bar 234 is threadingly adjusted in first clamping arm 222 with thumb screw 232 in the directions indicated by arrow 250, its distal end acts on second clamping arm 224 to pivot distal extensions 226, 228 of clamping arms 222, 224 toward or away from one another about intermediate joint 230. For example, adjusting drawbar 234 toward second clamping member 224 moves distal extensions 226, 228 toward one another to clamp anchor extensions 40 therebetween. Adjusting drawbar 234 away from second clamping member 224 moves distal extensions 226, 228 away from one another to release the anchor extensions 40 positioned therebetween.

Second clamping member 224 includes mounting posts 236 extending laterally therefrom. A coupling member 239 is rotatably mounted to posts 236 with a mounting pin 238. Coupling member 239 is movable by pivoting coupling member 239 relative to mounting assembly 221 in either direction about mounting pin 238 as indicated by arrows 252. Coupling member 239 further includes coupling portion 240 opposite mounting pin 238. A hinge pin 242 is rotatably received in coupling portion 240 and engaged to guide member 244. Guide member 244 is pivotal relative to coupling member 239 with hinge pin 242 as indicated by arrows 254.

Guide member 244 includes a guide portion 246 forming a guide passage therethrough that extends along guide axis 248. Guide instrument 220 is structured so that guide axis 248 intersects alignment axis 200 at any position of guide axis 248 relative to the anchor extensions 40 when guide instrument 200 is mounted to anchors extensions 40. For example, with coupling member 239 and guide member 244 each rotated fully clockwise, guide axis 248 is oriented in the position shown in FIG. 11, and in the position shown as guide axis 248' in FIG. 12. Coupling member 239 and guide member 244 can each be pivoted about their respective pivot axis to the fully extended position, shown in FIG. 12 and indicated therein as guide axis 248. Coupling member 239 and guide member 244 can further be pivoted counter-clockwise to locate guide axis on the side of extensions 40 opposite that shown in FIG. 11. Movement of coupling member 239 and guide member 244 can also locate guide axis 248 at any position between these positions and maintain guide axis 248 in intersection with alignment axis 200. The only limitations in positioning of guide member 244 and coupling member 239 are created by the contact of guide member 244 and/or coupling member 239 with one or both of mounting assembly 221 and anchor extensions 240.

After placement of the secondary anchor 10 into vertebra 24 with a guide instrument, it is contemplated that connecting element 90 may be installed and secured to anchors 10 with an inserter instrument such as shown in FIG. 10 and designated generally at 320. Inserter instrument 320 includes a configuration adapted for percutaneous placement of connecting element 90 in a two level stabilization procedure. Suitable inserter instruments and anchor extensions are also discussed in U.S. Pat. No. 6,530,929, which is incorporated herein by reference in its entirety.

Prior to mounting inserter instrument 320, a third anchor extension 40 is positioned through the path formed during placement of secondary anchor 10 and mounted to receiver portion 14 of secondary anchor 10. The third anchor extension 40 is manipulated through the skin and tissue of the patient and positioned between and coupled to the anchor extensions 40 extending from the primary anchors 10. Coupling of the proximal portions 44 to one another aligns the passages 16 of the multi-axial receiver portions 14 along alignment axis 200.

Support arms 322 of inserter instrument 320 are then rotatably mounted to the laterally oriented sidewalls 45 of primary anchor extensions 40 and clamped thereto via clamping mechanism 321. Inserter instrument 320 includes a distal portion 324 transversely oriented to and extending from arms 322. Distal portion 324 includes an arm 331 curved along a radius that extends from the pivotal connection point of arms 322 with anchor extensions 40 to alignment axis 200.

Connecting element 90 is coupled to and extends from arm 331 adjacent a proximal connecting end 91 of connecting element 90, and has a sufficient length extending to a distal insertion end 92 for a two-level stabilization procedure. Connecting element 90 can be curved with a radius of curvature equal to the distance between passageways 16 of anchors 10 and a pivot axis of inserter instrument 320 about anchor extensions 40. Connecting element 90 is fixed on inserter 324 and readied for percutaneous insertion into passageways 16 of anchors 10. Inserter instrument 320 swings about the pivot axis to move connecting element 90 toward receiver portions 14 along an extension of alignment axis 200, and thereby introducing leading end of connecting element 90 into the subject's body towards the aligned passages 16 of anchors 10. Connecting element 90 and inserter instrument 320 are further pivoted to pass portions of connecting element 90 through passages 16 of anchors 10 and finally position connecting element along alignment axis 200 and within receiver portions 14.

Connecting element 90 is placed through passages 16 of anchors 10 to a desired position, which can be confirmed radiographically or with any known imaging technique. Set screws associated with each anchor 10 can be driven downwardly through passages 46 of anchor extensions 40 to contact connecting element 90 and seat it in receiver portions 14 of anchors 10. Arm 331 can then be uncoupled from connecting element 90 and removed from the patient by swinging inserter instrument 320 back along path in which it was inserted. Inserter 324 is removed from anchor extensions 40, and anchor extensions 40 are uncoupled from one another. Anchor extensions 40 are then removed from the patient.

In one specific application, connecting element 90 is installed to stabilize a three vertebrae 22, 24, 26 after placement of one or more implants into one or more of the disc spaces 28, 30. The method can include removing intervertebral disc material from the space between vertebral bodies and/or introducing an implant into the disc space. Implant can be one or more interbody fusion devices, support members, artificial disc devices, annulus repair devices, and/or artificial ligaments. If desired, the anchor extensions 40 can be manipulated by the surgeon to apply a load to compress or distract the vertebrae prior to engaging connecting element 90 to anchors 10. In some surgical procedures, it may be desirable to insert one or more additional connecting elements for stabilization along the same vertebral levels, or along different vertebral levels.

Connecting element 90 can be an elongated rod or shaft curved along its length between connecting end 91 and insertion end 92. However, it should be understood that it is contemplated that connecting element 90 can include any configuration known for a rod, plate, implant, or fastener, so long as connecting element 90 is engageable to the bony segment. Further, connecting element 90 can be elastic or super-elastic member in the form of a cable, band or artificial ligament that used in tethering or other surgical procedures. Connecting element 90 can be percutaneously or non-percutaneously inserted with an inserter instrument, or with a freehand technique.

One specific example of a suitable anchor 10 is a multi-axial screw such as described in U.S. Pat. Nos. 5,797,911 and 5,879,350, each of which is incorporated herein by reference. Other examples for anchors 10 include uni-axial screws, bolts, clamps, hooks, and pins, for example. It is further contemplated that one or more of the anchors can include a multi-axial head and one or more of the other anchors include an uni-axial head. The anchors can be cannulated to facilitate placement over a guidewire and into the vertebra in minimally invasive procedures, or can be non-cannulated. Cannulated anchors can further include one or more fenestrations or openings for placement of bone cement or other material therethrough.

Pre-operative planning and image guided navigation of anchor placement and installation of connecting element 90 are also contemplated. The surgical techniques can employ any type of known imaging system to determine and locate optimum placement and orientation of the anchors in the bony structure and, if necessary, to locate skin locations for percutaneous puncture entry of the anchors and connecting element.

Primary anchor insertion can be monitored using any known viewing instrument or apparatus, and performed under any known surgical technique. For example, primary anchors 10 can be placed through a cannula or sleeve inserted through the skin that forms a working channel to the anchor location over the target bone. Anchor placement into the bony structure can be monitored endoscopically, microscopically, fluoroscopically, radiographically and/or with naked eye visualization through the cannula. Primary anchor placement can also be performed through micro-incisions, or through open incisions in which the skin and tissue is retracted to expose the bony structure.

In one specific technique for placing primary anchors 10, a guidewire of sufficient length is inserted percutaneously and anchored to the bony structure, such as a pedicle of the vertebra. The guidewire is coupled to a trackable instrument that is tracked via an image guided surgical system that generates a display on a computer monitor. With the guidewire secured at the appropriate location on the bony structure, various instruments for preparing and inserting the screw into the bony structure can be guided by the guidewire. The preparation and insertion can be monitored via a tracking instrument coupled to the various preparation and insertion instruments. After mounting anchor extensions to the engaged primary anchors, a guide instrument is mounted to the anchor extensions to guide placement of the secondary anchor at a desired trajectory into the pedicle located between the pedicles engaged by the primary anchors.

Connecting elements can be engaged on both sides of midline M of the spine, and along one or more levels of the spine. The connecting element can be engaged to stabilize adjacent vertebra in conjunction with any minimally invasive or open surgical techniques for placement of one or more implants into a disc space. For example, one or more interbody fusion devices or intervertebral spacers may be inserted into the disc space via an anterior, anterior oblique, lateral, postero-lateral, or transforaminal approach, and connecting element 90 can be positioned and engaged to the spinal column segment from a posterior approach. Further, connecting element 90 can be used to stabilize adjacent vertebrae, or any other bony structure, without placement of implants between structures comprising bony segment 20.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A system for placement of an anchor in an animal subject, comprising:
    a pair of anchor extensions engageable to the animal subject, each anchor extension including a proximal end and a distal end, said distal ends forming an alignment axis therebetween when engaged to the animal subject; and
    a guide instrument mountable adjacent said proximal ends of said pair of anchor extensions, said guide instrument including a guide member defining a guide axis intersecting said alignment axis when mounted to said pair of anchor extensions, wherein said guide member is rotatable around said proximal ends of said anchor extensions while mounted thereto to reposition said guide axis relative to said anchor extensions while maintaining said guide axis in intersecting relation with said alignment axis, wherein said guide instrument includes a mounting assembly coupled with said guide member, said mounting assembly being removably mounted to said pair of anchor extensions and said mounting assembly includes a mounting member and a coupling member rotatably mounted to and extending proximally from said mounting member, said mounting member being removably mounted between said pair of anchor extensions along a mounting axis, wherein said guide member is coupled to said coupling member at a hinge, and said hinge is offset proximally from said proximal ends of said pair of anchor extensions so that coupling member is rotatable 360 degrees around said mounting member when said mounting member is mounted between said pair of anchor extensions.

2. The system of claim 1, further comprising an inserter including a proximal portion pivotally mountable adjacent said proximal ends of said pair of anchor extensions and a distal portion extending transversely to said proximal portion, said distal portion being movable about said proximal ends of said pair of anchor extensions by pivoting said proximal portion relative thereto.

3. The system of claim 2, further comprising a connecting element releasably engageable to said distal portion of said inserter, said connecting element being positionable along said alignment axis with said inserter.

4. The system of claim 3, wherein said connecting element is a rod.

5. The system of claim 3, further comprising a pair of anchors each including a distal portion engageable to a bony segment of the animal subject, said pair of anchors further each including a proximal receiver portion defining a passageway alignable along the alignment axis, said pair of anchor extensions being mountable with a corresponding one of said receiver portions of said anchors.

6. The system of claim 5, wherein said pair of anchors are multi-axial screws.

7. The system of claim 1, wherein said coupling member is removably mounted to said mounting member.

8. The system of claim 1, wherein said guide member is pivotally coupled to said coupling member about a hinge axis offset from said mounting axis.

9. The system of claim 8, wherein said guide member includes a bore extending along said guide axis.

10. The system of claim 1, wherein said coupling member is rotatably and removably coupled to said mounting member with a mounting pin extending through a bore of said mounting member, said bore extending along said mounting axis.

11. A system for placement of an anchor in an animal subject, comprising:
a pair of anchor extensions engageable to the animal subject, each anchor extension including a proximal end and a distal end, said distal ends forming an alignment axis therebetween when engaged to the animal subject;
a guide instrument mountable adjacent said proximal ends of said pair of anchor extensions, said guide instrument including a guide member defining a guide axis intersecting said alignment axis when mounted to said pair of anchor extensions, wherein said guide member is rotatable around said proximal ends of said anchor extensions while mounted thereto to reposition said guide axis relative to said anchor extensions while maintaining said guide axis in intersecting relation with said alignment axis, wherein said guide instrument includes a mounting assembly coupled with said guide member, said mounting assembly being removably mounted to said pair of anchor extensions and said mounting assembly includes a mounting member and a coupling member rotatably mounted to and extending proximally from said mounting member, said mounting member being removably mounted between said pair of anchor extensions alone a mounting axis, wherein:
said coupling member is rotatably and removably coupled to said mounting member with a mounting pin extending through a bore of said mounting member, said bore extending along said mounting axis; and
said mounting pin includes a distal portion positionable in said bore, said distal portion including a pair of longitudinal fingers and a slot between said fingers.

12. The system of claim 11, wherein said pair of fingers each include a radial projection engageable to said mounting member when said mounting pin is positioned through said bore.

13. A system for placement of an anchor in an animal subject, comprising:
a pair of anchor extensions engageable to the animal subject, each anchor extension including a proximal end and a distal end, said distal ends forming an alignment axis therebetween when engaged to the animal subject; and
a guide instrument mountable adjacent said proximal ends of said pair of anchor extensions, said guide instrument including a guide member defining a guide axis intersecting said alignment axis when mounted to said pair of anchor extensions, wherein said guide member is rotatable around said proximal ends of said anchor extensions while mounted thereto to reposition said guide axis relative to said anchor extensions while maintaining said guide axis in intersecting relation with said alignment axis, wherein said guide instrument includes a mounting assembly coupled with said guide member, said mounting assembly being removably mounted to said pair of anchor extensions and said mounting assembly is positionable about said proximal ends of said pair of anchor extensions and clampable thereto and said guide instrument includes a coupling member rotatably coupled to said mounting assembly adjacent said proximal end of one of said anchor extensions, said coupling member extending from said rotatable connection with said mounting assembly to a coupling portion, said guide member being rotatably coupled to said coupling portion of said coupling member wherein said guide member is coupled to said coupling member at a hinge, and said hinge is offset proximally from said proximal ends of said pair of anchor extensions so that coupling is rotatable 360 degrees around said mounting member when said mounting member is mounted between said pair of anchor extensions.

14. A system for placement of an anchor in an animal subject, comprising:
a pair of anchor extensions engageable to the animal subject, each anchor extension including a proximal end and a distal end, said distal ends forming an alignment axis therebetween when engaged to the animal subject;
a guide instrument mountable adjacent said proximal ends of said pair of anchor extensions, said guide instrument including a guide member defining a guide axis intersecting said alignment axis when mounted to said pair of anchor extensions, said guide member being movable relative to said pair of anchor extensions while maintaining said guide axis in intersecting relation with said alignment axis, wherein said guide instrument includes a mounting assembly coupled with said guide member, wherein:
said mounting assembly is removably mounted to said pair of anchor extensions;
said mounting assembly includes a mounting member and a coupling member rotatably mounted to and extending proximally from said mounting member with said mounting member being removably mounted between said pair of anchor extensions along a mounting axis; and
said guide member is coupled to said coupling member at a location offset proximally of said proximal ends of said anchor extensions to permit said guide member to rotate 360 degrees around said mounting member when said mounting member is mounted between said pair of anchor extensions.

15. The system of claim 14, wherein said coupling member is removably mounted to said mounting member.

16. The system of claim 14, wherein said guide member is pivotally coupled to said coupling member about a hinge axis offset from said mounting axis.

17. The system of claim 16, wherein said guide member includes a bore extending along said guide axis.

18. The system of claim 14, wherein said coupling member is rotatably and removably coupled to said mounting member with a mounting pin extending through a bore of said mounting member, said bore extending along said mounting axis.

19. The system of claim 14, further comprising an inserter including a proximal portion pivotally mountable adjacent said proximal ends of said pair of anchor extensions and a distal portion extending transversely to said proximal portion, said distal portion being movable about said proximal ends of said pair of anchor extensions by pivoting said proximal portion relative thereto.

20. The system of claim 19, further comprising a connecting element releasably engageable to said distal portion of said inserter, said connecting element being positionable along said alignment axis with said inserter.

21. The system of claim 20, wherein said connecting element is a rod.

22. The system of claim 21, further comprising a pair of anchors each including a distal portion engageable to a bony segment of the animal subject, said pair of anchors further each including a proximal receiver portion defining a passageway alignable along the alignment axis, said pair of anchor extensions being mountable with a corresponding one of said receiver portions of said anchors.

23. The system of claim 22, wherein said pair of anchors are multi-axial screws.

24. A system for placement of an anchor in an animal subject, comprising:
a pair of anchor extensions engageable to the animal subject, each anchor extension including a proximal end and a distal end, said distal ends forming an alignment axis therebetween when engaged to the animal subject;
a guide instrument mountable adjacent said proximal ends of said pair of anchor extensions, said guide instrument including a guide member defining a guide axis intersecting said alignment axis when mounted to said pair of anchor extensions, said guide member being movable relative to said pair of anchor extensions while maintaining said guide axis in intersecting relation with said alignment axis, wherein said guide instrument includes a mounting assembly coupled with said guide member, wherein:
said mounting assembly is removably mounted to said pair of anchor extensions;
said mounting assembly includes a mounting member and a coupling member rotatably mounted to and extending proximally from said mounting member with said mounting member being removably mounted between said pair of anchor extensions along a mounting axis;
said coupling member is rotatably and removable coupled to said mounting member with a mounting pin extending through a bore of said mounting member, said bore extending along said mounting axis; and
said mounting pin includes a distal portion positionable in said bore, said distal portion including a pair of longitudinal fingers and a slot between said fingers.

25. The system of claim 24, wherein said pair of fingers each include a radial projection engageable to said mounting member when said mounting pin is positioned through said bore.

26. A system for placement of an anchor in an animal subject, comprising:
a pair of anchor extensions engageable to the animal subject, each anchor extension including a proximal end and a distal end, said distal ends forming an alignment axis therebetween when engaged to the animal subject; and
a guide instrument mountable adjacent said proximal ends of said pair of anchor extensions, said guide instrument including a guide member defining a guide axis intersecting said alignment axis when mounted to said pair of anchor extensions, said guide member being movable relative to said pair of anchor extensions while maintaining said guide axis in intersecting relation with said alignment axis, wherein said guide instrument includes a mounting assembly coupled with said guide member and said mounting assembly is removably mounted to and positionable about said proximal ends of said pair of anchor extensions and clampable thereto, wherein said guide instrument includes a coupling member rotatably coupled to said mounting assembly adjacent said proximal end of one of said anchor extensions, said coupling member extending from said rotatable connection with said mounting assembly to a coupling portion, said guide member being rotatably coupled to said coupling portion of said coupling member wherein said guide member is coupled to said coupling member at a hinge, and said hinge is offset proximally from said proximal ends of said pair of anchor extensions so that coupling is rotatable 360 degrees around said mounting member when said mounting member is mounted between said pair of anchor extensions.

27. The system of claim 26, further comprising an inserter including a proximal portion pivotally mountable adjacent said proximal ends of said pair of anchor extensions and a distal portion extending transversely to said proximal portion, said distal portion being movable about said proximal ends of said pair of anchor extensions by pivoting said proximal portion relative thereto.

28. The system of claim 27, further comprising a connecting element releasably engageable to said distal portion of said inserter, said connecting element being positionable along said alignment axis with said inserter.

29. The system of claim 28, wherein said connecting element is a rod.

30. The system of claim 28, further comprising a pair of anchors each including a distal portion engageable to a bony segment of the animal subject, said pair of anchors further each including a proximal receiver portion defining a passageway alignable along the alignment axis, said pair of anchor extensions being mountable with a corresponding one of said receiver portions of said anchors.

31. The system of claim 30, wherein said pair of anchors are multi-axial screws.

32. A system for placement of an anchor in an animal subject, comprising:
a pair of anchor extensions engageable to the animal subject, each anchor extension including a proximal end and a distal end, said distal ends forming an alignment axis therebetween when engaged to the animal subject; and
a guide instrument mounted to said anchor extensions adjacent to said proximal ends of said pair of anchor extensions, said guide instrument including a guide member defining a guide axis intersecting said alignment axis when mounted to said pair of anchor extensions, wherein said guide member is movable relative to said proximal ends of said anchor extensions while mounted thereto to reposition said guide axis relative to said anchor extensions while maintaining said guide axis in intersecting relation with said alignment axis, wherein said guide instrument includes a mounting assembly coupled with said guide member, said mounting assembly being removably mounted to said pair of anchor extensions and said mounting assembly includes a mounting member and a coupling member rotatably mounted to and extending proximally from said mounting member, said mounting member being removably mounted between said pair of anchor extensions along a mounting axis, wherein said guide member is coupled to said coupling member at a location offset proximally of said proximal ends of said anchor extensions to permit said guide member to rotate 360 degrees around said mounting member when said mounting member is mounted between said pair of anchor extensions.

33. The system of claim 32, wherein said coupling member is removably mounted to said mounting member.

34. The system of claim 32, wherein said guide member is pivotally coupled to said coupling member about a hinge axis offset from said mounting axis.

35. The system of claim 34, wherein said guide member includes a bore extending along said guide axis.

36. The system of claim 32, wherein said coupling member is rotatably and removably coupled to said mounting member with a mounting pin extending through a bore of said mounting member, said bore extending along said mounting axis.

37. A system for placement of an anchor in an animal subject, comprising:
a pair of anchor extensions engageable to the animal subject, each anchor extension including a proximal end and a distal end, said distal ends forming an alignment axis therebetween when engaged to the animal subject;
a guide instrument mounted to said anchor extensions adjacent to said proximal ends of said pair of anchor extensions, said guide instrument including a guide member defining a guide axis intersecting said alignment axis when mounted to said pair of anchor extensions, wherein said guide member is movable relative to said proximal ends of said anchor extensions while mounted thereto to reposition said guide axis relative to said anchor extensions while maintaining said guide axis in intersecting relation with said alignment axis, wherein said guide instrument includes a mounting assembly coupled with said guide member, said mounting assembly being removably mounted to said pair of anchor extensions and said mounting assembly includes a mounting member and a coupling member rotatably mounted to and extending proximally from said mounting member, said mounting member being removably mounted between said pair of anchor extensions along a mounting axis, wherein:
said coupling member is rotatably and removably coupled to said mounting member with a mounting pin extending through a bore of said mounting member, said bore extending along said mounting axis; and
said mounting pin includes a distal portion positionable in said bore, said distal portion including a pair of longitudinal fingers and a slot between said fingers.

38. A system for placement of an anchor in an animal subject, comprising:
a pair of anchor extensions engageable to the animal subject, each anchor extension including a proximal end and a distal end, said distal ends forming an alignment axis therebetween when engaged to the animal subject; and
a guide instrument mounted to said anchor extensions adjacent to said proximal ends of said pair of anchor extensions, said guide instrument including a guide member defining a guide axis intersecting said alignment axis when mounted to said pair of anchor extensions, wherein said guide member is movable relative to said proximal ends of said anchor extensions while mounted thereto to reposition said guide axis relative to said anchor extensions while maintaining said guide axis in intersecting relation with said alignment axis, wherein said guide instrument includes a mounting assembly coupled with said guide member, said mounting assembly being removably mounted to said pair of anchor extensions and said mounting assembly is positionable about said proximal ends of said pair of anchor extensions and clampable thereto and said guide instrument includes a coupling member rotatably coupled to said mounting assembly adjacent said proximal end of one of said anchor extensions, said coupling member extending from said rotatable connection with said mounting assembly to a coupling portion, said guide member being rotatably coupled to said coupling portion of said coupling member wherein said guide member is coupled to said coupling member at a hinge, and said hinge is offset proximally from said proximal ends of said pair of anchor extensions so that coupling is rotatable 360 degrees around said mounting member when said mounting member is mounted between said pair of anchor extensions.

* * * * *